United States Patent [19]

Suhonen

[11] Patent Number: 5,380,198

[45] Date of Patent: Jan. 10, 1995

[54] MATRIX FOR DENTAL MEDICINE AND A DEVICE FOR THE FABRICATON OF MATRIX BANDS

[76] Inventor: Jouko Suhonen, Huswisenstrasse 7, CH-8426 Lufingen, Switzerland

[21] Appl. No.: 971,756

[22] PCT Filed: Aug. 5, 1991

[86] PCT No.: PCT/EP91/01471

§ 371 Date: Feb. 8, 1993

§ 102(e) Date: Feb. 8, 1993

[87] PCT Pub. No.: WO92/02189

PCT Pub. Date: Feb. 20, 1992

[30] Foreign Application Priority Data

Aug. 6, 1990 [CH] Switzerland ............. 2562/90-4
Dec. 28, 1990 [DE] Germany ............. 9017522

[51] Int. Cl.⁶ ............. A61C 5/04
[52] U.S. Cl. ............. 433/39
[58] Field of Search ............. 433/23, 39, 40, 149, 433/215

[56] References Cited

U.S. PATENT DOCUMENTS

| | | |
|---|---|---|
| 1,794,213 | 2/1931 | Spahn ............. 433/23 |
| 2,607,117 | 8/1952 | Baughan ............. 433/39 |
| 3,074,169 | 1/1963 | Freeman ............. 433/39 |
| 3,082,531 | 3/1963 | Jacobsen ............. 433/39 |
| 3,145,472 | 8/1964 | Tofflemire ............. 433/39 |
| 3,421,222 | 1/1969 | Newman ............. 433/39 |
| 3,842,505 | 10/1974 | Eames . |
| 4,523,909 | 6/1985 | Lazarus . |

FOREIGN PATENT DOCUMENTS

0241197A1 10/1987 European Pat. Off. .

Primary Examiner—Cary E. O'Connor
Assistant Examiner—Nicholas D. Lucchesi
Attorney, Agent, or Firm—Friedrich Kueffner

[57] ABSTRACT

The dental matrix (1) has at least one transparent region and its design is such that the marginal adaptation of approximal edge regions of light-cured MO, OD and MOD composite restorations is optimized.

8 Claims, 8 Drawing Sheets

Fig.12
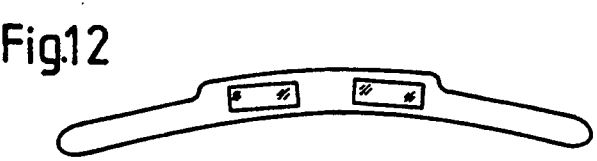
Fig.12b
Fig.12d
Fig.12f
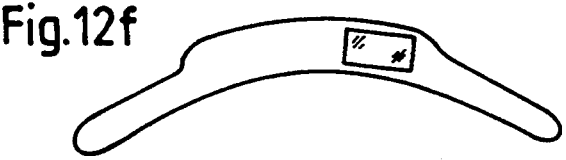
Fig.12h
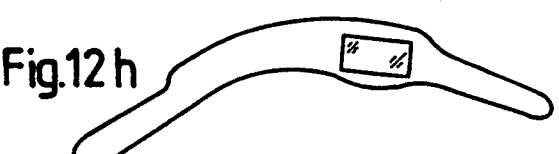
Fig.12j
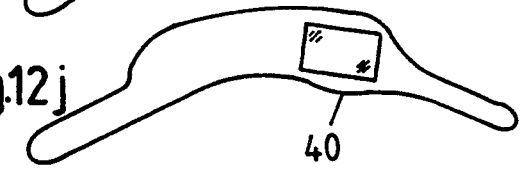
Fig.12a
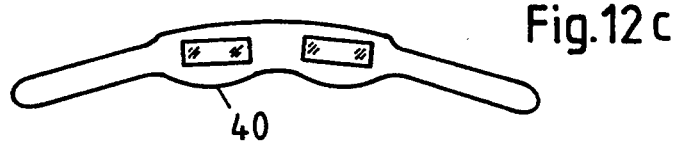
Fig.12c
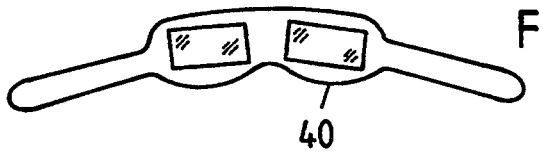
Fig.12e

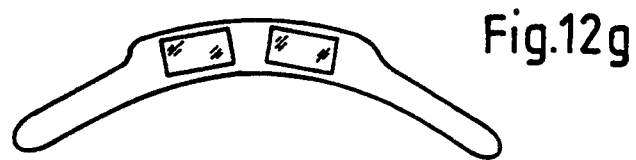
Fig.12g
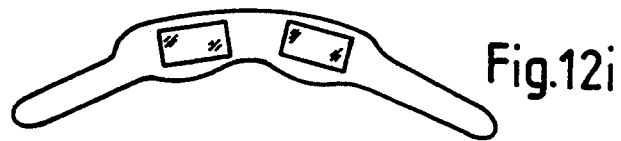
Fig.12i
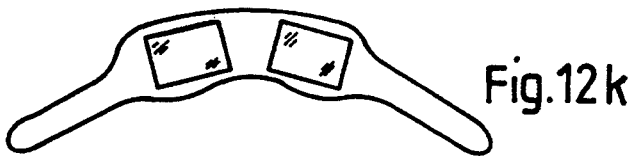
Fig.12k
Fig.13
Fig.14
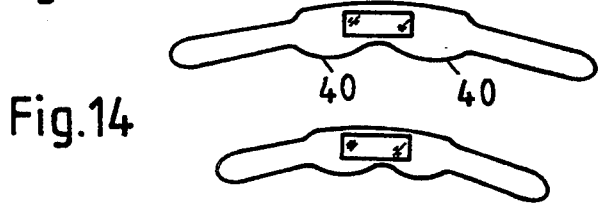
Fig.15
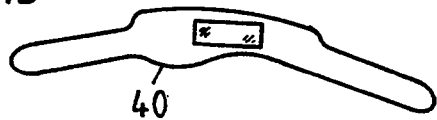
Fig.16
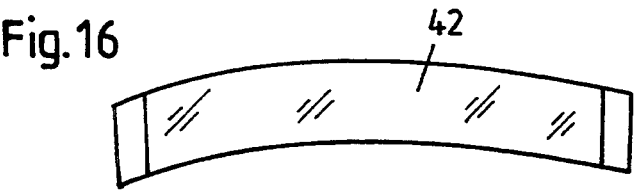

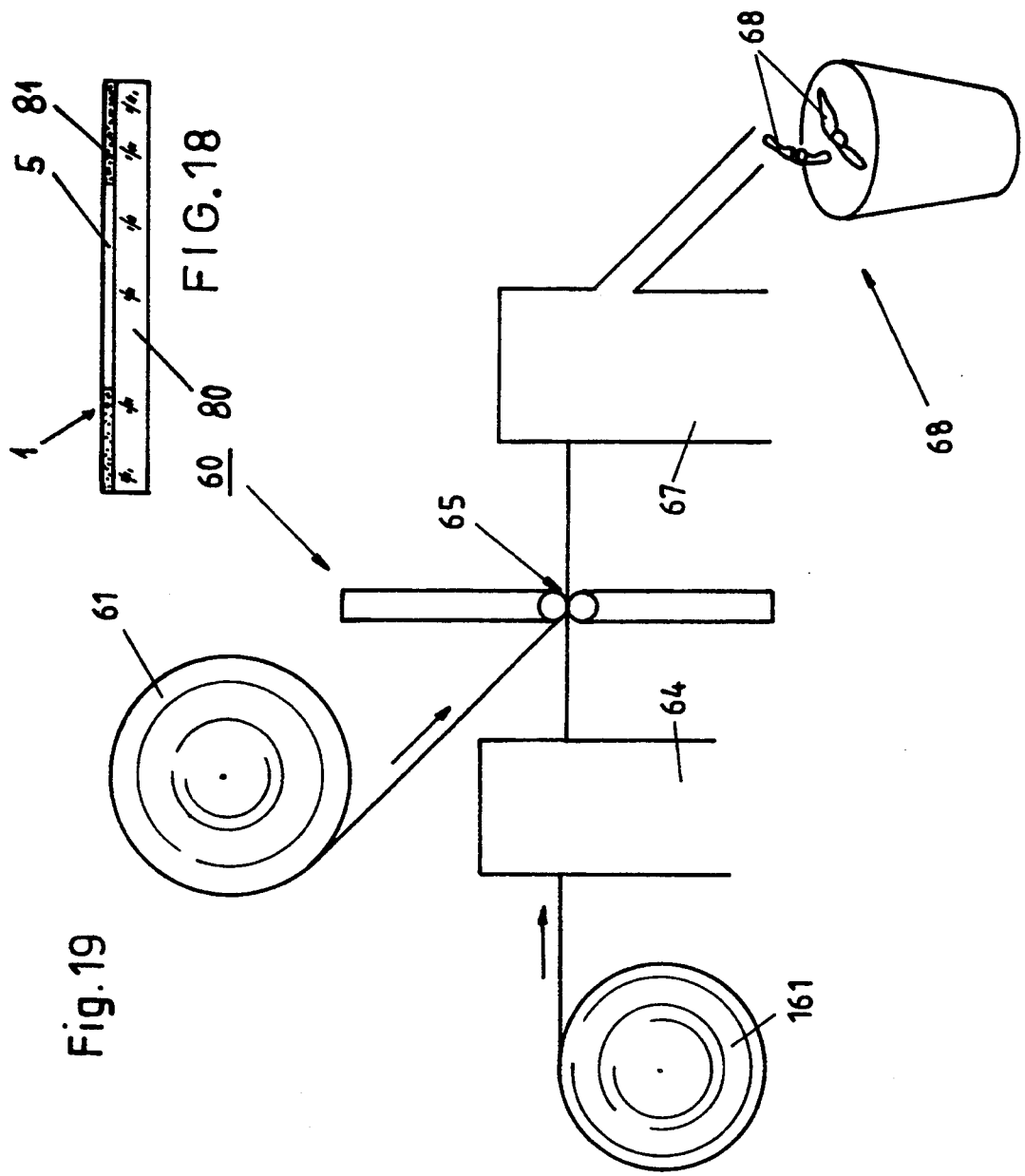

MATRIX FOR DENTAL MEDICINE AND A DEVICE FOR THE FABRICATON OF MATRIX BANDS

BACKGROUND OF THE INVENTION

1. Field of the Invention

The present invention relates to a matrix for dental medicine which serves as a formwork or shuttering when fillings are inserted into dental cavities and which comprises a band-like blank of a two-layer material, in which one layer is opaque and the other layer transparent, as well as a device for the fabrication of bands of matrices.

2. Description of the Related Art

The objects of the known, differently shaped matrices in the conserving dental medicine are as follows. It is the purpose of the matrices to supply walls lost through caries, due to abrasion and cavity preparation (elimination of caries) during the insertion of the filling into the cavity along the lines of a formwork or shuttering used in construction engineering. By way of a "female mold" it is the purpose of the matrix to restore the lost wall of the tooth —for the most part in Class II cavities—to make the accurate insertion of the filling possible and to secure the marginal termination cervically, i.e. within the area of the neck of the tooth. The subsequent filling then constitutes the "patrix" in a manner of speaking.

In dental medicine, increasing use is made of plastic as material for fillings. The same has to be cured on or in the tooth after having been inserted into the cavity, process which presents certain difficulties since the curing has to take place first within the lower areas in the proximity of the tooth since otherwise, when the free plastic portions located at the top, due to the shrinkage of the cured plastic materially, particularly within the internal contact areas of tooth and plastic, cracks or hollow spaces come into being.

The fundamental problem of the curing of plastic which is effected with the aid of Luminous energy and of supplying the same to the areas of the filling which are located below is solved by means of the so-called illuminating wedges which are capable of conveying or directing the incident light by deflection to the desired and, for the most part, hidden points.

However, what still presents a problem are the so-called matrices which not only have to make the geometrically as correct as possible filling of the cavities possible in the form of a formwork or shuttering, but also the curing of the inserted plastic while being mounted on the tooth.

From the U.S. Pat. No. 4,523,909, a matrix for the dental medicine is known which serves as a formwork when fillings are inserted into dental cavities. This matrix is comprised of a band-shaped blank of a metallic material; it consequently is opaque. This metallic blank on the side which faces the filling, is coated with a plastic film or sheeting which may be transparent or opaque, whereby, however, a transmittivity of light through the matrix is not achieved. The matrix itself does not possess any transparent area or a transparent window. Due to the circumstance that the matrix is comprised of opaque material, no possibility exists of employing plastic that is capable of being cured by light as material for the fillings.

SUMMARY OF THE INVENTION

That is why it is the object of the invention to provide a matrix for use in dental medicine of the type stated in the beginning which, along the lines of a framework or shuttering, makes a geometrically accurate filling of the cavities possible and, while mounted on the tooth, a perfect curing of the inserted plastic with the aid of light energy.

In accordance with the present invention, the matrix for dental medicine includes a band-shaped blank of transparent material with a positioning portion in a central area of the blank and two terminal areas connected to the two ends of the central area. The blank is provided with a vapor-deposited coating of opaque metallic material, layered over the blank of transparent material, with at least one window portion of the transparent material free of the metallic material coating, wherein the at least one window portion is located in the central area of the blank.

A window matrix constructed according to the invention allows the optimization of the marginal adaptation of approximal marginal areas of light-cured MO, OD or MOP composite restorations. This so-called "hardness changing method" through the window makes it possible to control the polymerization shrinkage: By means of the Laterally reflecting illuminating wedges it is possible, within the, with respect to the secondary is caries (recurrent caries), gingivitis (inflammation of the gingiva) and periodontitis (inflammation of the attachment apparatus), critical gingivo-approximal area, to optimize the marginal conditions thanks to the reversal of the shrinkage vectors.

This technique involving the use of window matrices not only eliminates the negative characteristics of the volume shrinkage due to the polymerization typical of composites, but also prevents the fine surpluses by tear-resistant tightening of the matrix band which, furthermore, can be tightened very hard without the risk of tearing.

Furthermore, the window matrix makes a surplus-free cementing down of the most widely varying adhesive restorations, such as BRILLINAT, CERAM, CEREC, DICOR, BOS, ISOSIT, MIRAGE and TUCERAM inlays possible.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWINGS

Embodiments of the invention are explained in greater detail below with the aid of the drawings. Thus:

FIGS. 12, 12a to 12k show a further plurality of matrix configurations in different embodiments for molars;

FIGS. 13 to 15 show single-bulge and double-bulge basic forms of metal matrix bands;

FIG. 16 shows a band comprised of a plastic possessing a crystal-clear transparency in the uncoiled state;

FIG. 18 shows an enlarged vertical section of a matrix fabricated from a metal-coated plastic film or sheet, and FIG. 19 shows a diagrammatical representation of a device for fabricating dental matrices.

DETAILED DESCRIPTION OF THE EMBODIMENTS

Figure 1:
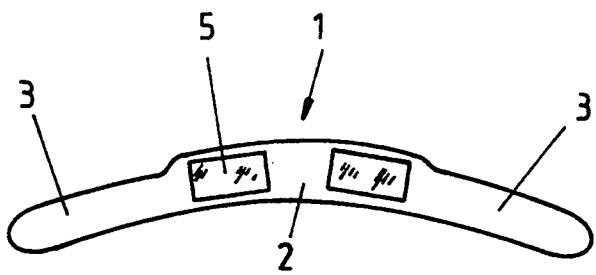
FIG. 1 shows a view from above of a matrix such as is employed for double approximal fillings and relatively wide interdental gaps.

The matrix 1 depicted in FIG. 1, within its central area, is provided with a positioning portion 2 which, on both sides, is followed by two terminal areas 3 which, with respect to the positioning part 2, are stepped in such a way that the positioning part 2 projects with a section from the plane formed by the upper edges of the two terminal areas 3. The matrix 1 is provided with two stamped-out windows 5; it is preferably constructed in two layers, in which case the one supporting layer comprises a thin steel band of e.g. 0.05 mm thickness, upon which an equally thin, transparent strip of plastic, by way of preference of cellulose acetate, is attached. The two layers may be bonded to each other, be thermally sealed by warmth or heat or be joined together in some other way; when in use, they form a unit, in which case the plastic strip rests against the dental filling and the steel band is at a distance from said filling, as is illustrated e.g. in FIG. 5.

Figure 2:
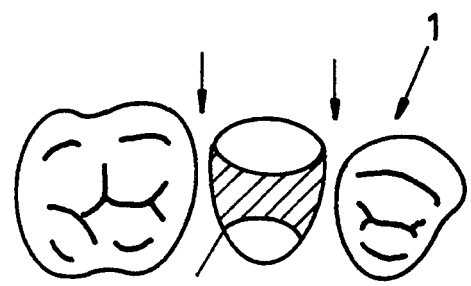
FIG. 2 shows a view from above of three teeth spaced a considerable distance apart from each other.
Figure 3:
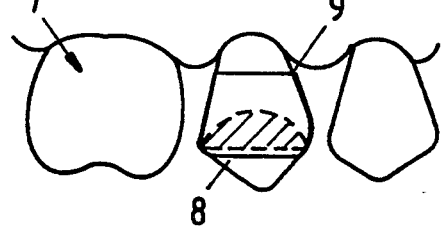
FIG. 3 shows a side view of the teeth according to FIG. 2.

The FIGS. 2 and 3 show, in a top view and in a side view, a dental group 7 comprising three teeth, of which the center tooth has a cavity 8 which has to be filled with a plastic while the original shape of the tooth is adhered to. Within the area of the dental neck 9, as is apparent from FIG. 3, the circumference of the tooth decreases. It is for this reason that the matrix, when engaging around the tooth to be treated and when the matrix is contracted at its two ends 3, has to produce a conical shape in order to encircle the dental configuration tightly which, at the point of contact, is broader.

That is why the wall edge towards the cervical area is shorten than the edge which faces the marginal strip of the filling, as is disclosed by FIG. 3. The matrix 1 reproduces the anatomical configuration of the tooth within the cervical area, i.e. within the area of the dental neck, as accurately as possible. It thereby prevents the excessive filling with filling material within this area and thus protects the marginal parodontium. In order to resist the lateral forces occurring during the insertion of the filling material, the matrix 1 is equipped with the steel band.

Figure 4:
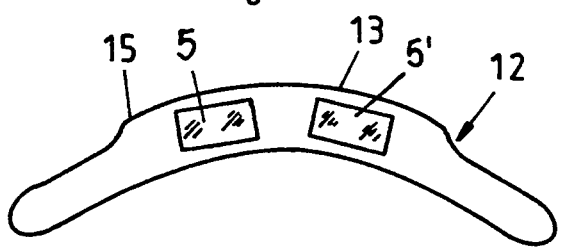
FIG. 4 shows a matrix for the purpose according to FIG. 1 for adjacent teeth.
Figure 5:
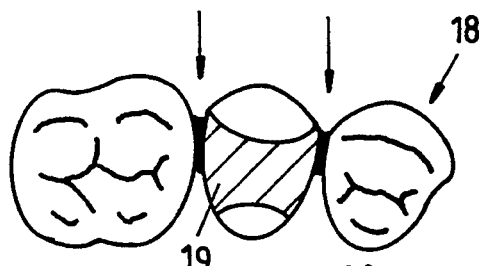
FIG. 5 shows a view from above of adjacent teeth.
Figure 6:
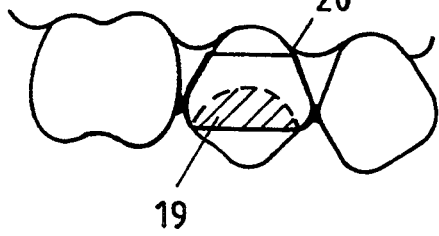
FIG. 6 shows a side view of the teeth according to FIG. 5

The FIGS. 4 to 6 depict analogous representations as do the FIGS. 1 to 3, but of closely set teeth and with a small diameter of the dental neck of the tooth to be tretaed. In this embodiment, the matrix band should Likewise project cervically only a little above the approximal box in order to be wedged there. This wedging is shown particularly in FIG. 7 on an enlarged scale.

The FIG. 4 shows a matrix 12 having a curvature 13 which is greater than that of the matrix 1 according to FIG. 1, as well as with two windows 5, 5' and a pronounced conical stepping 15 which corresponds to the smaller circumference of the dental neck.

This matrix 12 is intended to be used on a dental group 18 in which the center tooth has a cavity and a, in diameter, relatively small dental neck 20. The matrix according to FIG. 4 allows for this configuration by the relatively large conical stepping 15.

Figure 7:
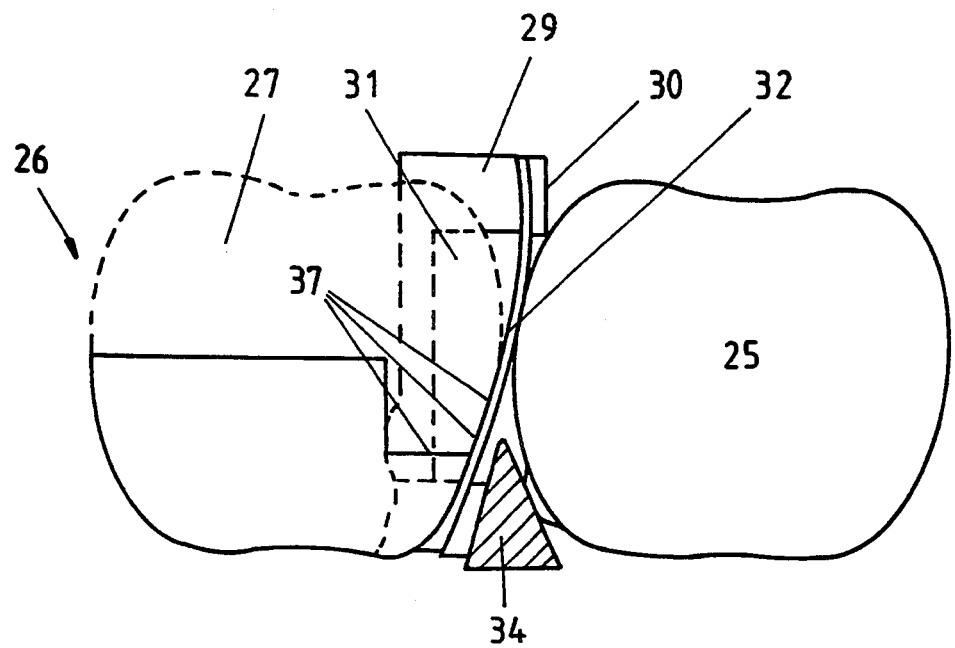
FIG. 7 shows a side view of closely adjacent teeth with inserted matrix and an illuminating wedge.

In FIG. 7, two teeth are illustrated in a side view, viz. a sound tooth 25 and a tooth 26 with a cavity provided with a plastic filling 27 which is indicated in a dash-dotted manner. A matrix 28 of the type described has an externally located steel band 30 with one or several windows 31 and a plastic band 32 resting against the tooth to be treated 26. An illuminating wedge 34 is inserted between the dental necks of the teeth 25 and 26.

Figure 8:
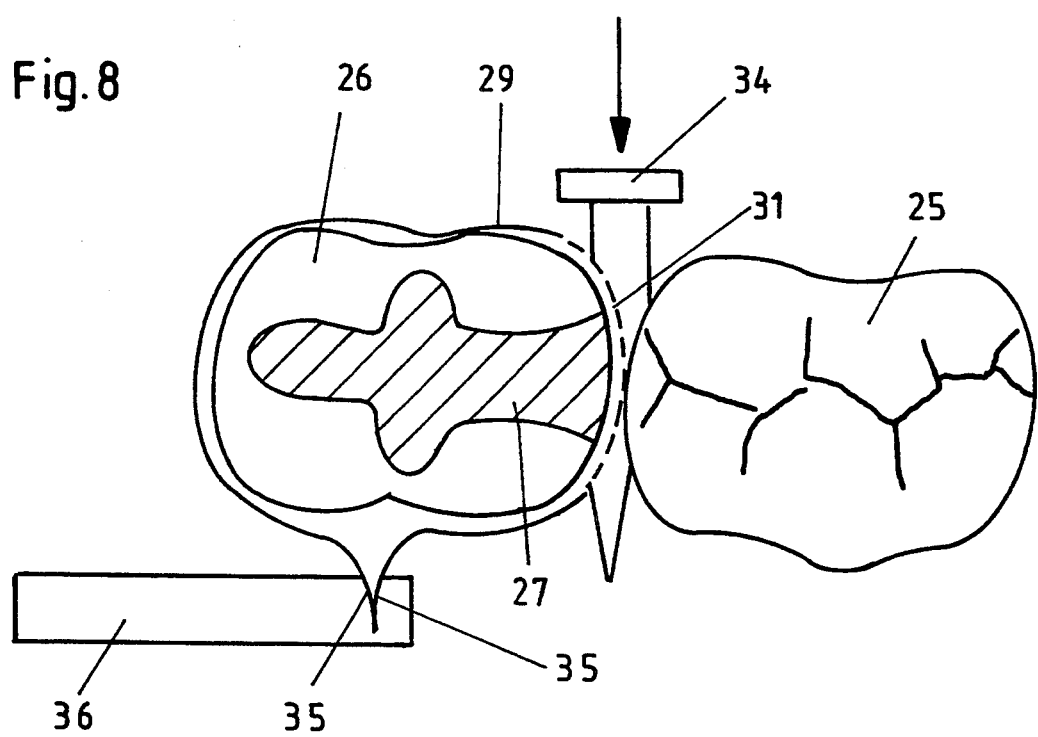
FIG. 8 shows a view from above of a pair of teeth according to FIG. 7 with an inserted illuminating wedge and a matrix tightener.
Figure 9:
FIGS. 9, 9a to 9e and FIGS. 10, 10a to 10e show a number of varying matrix configurations for use with individual dental positions and plastic fillings.
Figure 9B:
Figure 9D:
Figure 9A:
Figure 9C:
Figure 9E:
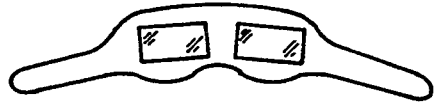
Figure 10:
Figure 10B:
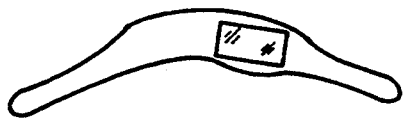
Figure 10D:
Figure 10A:
Figure 10C:
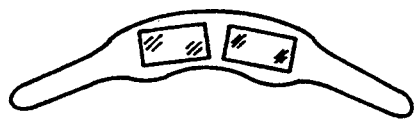
Figure 10E:
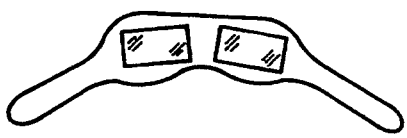
Figure 11:
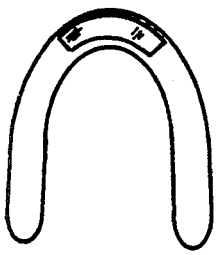
FIG. 11 shows a matrix with a window within the dental neck area.

The FIG. 8 shows the top view of the teeth according to the arrangement according to FIG. 7, in which case the two matrix ends 35 of the matrix laid around the tooth to be treated 26 are tightened with the aid of a matrix tightener 36 around the tooth by the matrix ends being seized and whereby the filling is imparted the shape desired in the FIGS. 7 and 8. The lighting of the illuminating wedge 34 by means of an external light source permits, in this position of the parts, to cure the critical area where plastic and dental material meet as the first within the primary curing area 37 and to thereby prevent the feared shrinkage interstices between the plastic and the dental material. The areas of the plastic material which are located at the top are cured subsequently in such a way that the shrinkage of the curing manifests itself only on the free areas of the plastic and, basically, the entire plastic material can be cured so as to be devoid of the formation of any cracks or interstices.

The matrix has, dependent upon the application indication, one (for single approximal fillings) or two windows (for double approximal fillings) of cellulose acetate within the approximal area. The windows make a perfect light curing within the approximal area possible. The action of the light is not restricted.

The matric band is retained in position with the aid of matrix tighteners, such as the TOFFEL wire system, the UHM system or the NYSTROM I and II system.

The FIGS. 9, 9a to 9e and 10, 10a to 10e show premolar matrix bands, while the FIGS. 12, 12a to 12k show molar matrix bands. The bulges 40 are clearly perceptible.

The FIGS. 13 and 14 show the basic form of double-bulge matrix bands, while FIG. 15 discloses a single-bulge embodiment. In this case the window sizes of molar bands are approximately 5×10 mm and the premolar bands possess a window size of approximately 4×8 mm.

The FIG. 16 shows a cellulose acetate strip 42, such as is applied prior to the stamping out of the matrix with the steel band and subsequent to the windows being stamped out.

Figure 17:
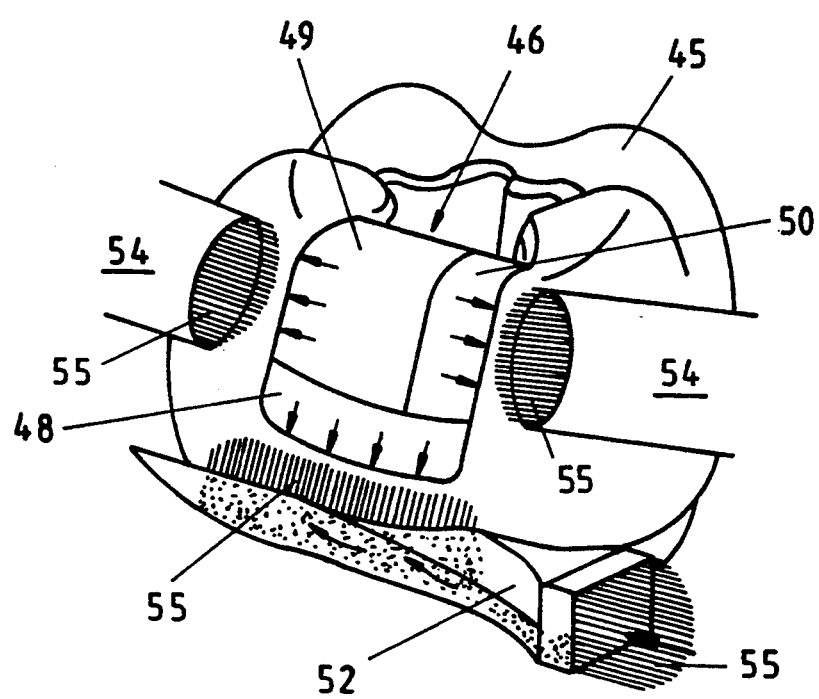
FIG. 17 shows a diagrammatical representation of a tooth provided with a filling having consecutive curing areas.

FIG. 17 shows a tooth 45 in perspective representation provided with a filling 46 which is schematically boldly framed and identified with zones 48, 49 and 50. An illuminating wedge 52 is acted upon by a light source with light beams 55 which, owing to the construction of the wedge, are deflected and thus cure the lowermost zone 48 when light is incident.

Subsequently the two zones 49 and 50, as is apparent in a diagrammatically shown manner, are finally cured, in which case the matrices shown in the various figures appropriately encircle the plastic filling 46 so that the same can be subjected to the curing process in a geometrically correct manner.

In FIG. 19, a device 60 for the fabrication of matrix bands is diagrammatically illustrated which comprises a plastic band roll 61 and a metal band roll 161. The metal band of the steel band roll 161 is passed through a stamping means, by means 64 of which the pertinent number of windows is stamped out. The plastic band is removed from the roll and the stamped-out metal bands are laminated to each other in the joining station 65 by heat, adhesive or suchlike so that they are able to form an inseparable unit. The two combined bands are conveyed into a matrix punch 67, with the aid of which the matrices 68 are fabricated and ejected possesing a form in which they are ready for use. The metal band imparts the requisite rigidity to the window matrices, which again is of advantage when the band is laid as well as in the shaping the filling.

According to one of the embodiments, the matrix 1 is comprised of a thin band-shaped blank of steel or some other suitable material, it being also possible to employ plastics which do not react with the dental filling. In this band-like metallic blank, one or several window-like perforations 5 are formed which, by means of a strip-shaped blank, are covered by means of a transparent, more particularly, crystal-clear plastic, said plastic strip possessing a design which corresponds to the shape and dimensions of the steel band of the matrix 1 so that the plastic strip coincides fully with the steel band. However, the possibility also exists of disposing blanks of transparent plastic solely within the area of the window 5 in the steel band, in which case these plastic bands are dimensioned in such a way that the windows 5 are covered and that they rest with a section against the wall area of the steel band so as to make it possible to attach the plastic blanks to the steel band. As covering for the windows 5, transparent plastic are employed, such as e.g. plastics having a cellulose base, such as cellulose acetate, or vinyl polymerisates, PS, PMMA and PC.

According to a further embodiment, the matrix provided with at least one window 5 is comprised of a blank constructed according to the configuration of the matrix fabricated from a transparent, crystal-clear plastic, e.g. possessing a cellulose base, such as cellulose acetate, or a vinyl polymerisate, PS, PMMA and PC, in which case especially such plastics are employed as are used for optical purposes, in which a certain elasticity has to be present so as to enable one to lay the matrix around a tooth. For the formation of windows 5, the matrix of the plastic strip is provided with a metallic coating which may e.g. be vapor-deposited while window-like areas are formed. Metallized plastics of this type are produced by non-galvanic or by galvanic processes. Consequently, the fabrication may be effected in accordance with the metallization process, in which low-melting metals are applied to the plastic in the form of a mist or according to the metal reduction method, in which metal salt solutions, e.g. gold, silver or copper salt solutions are reduced with the aid of formaldehyde. The materials then precipitate onto the plastic. A metal coating is also possible to effect in accordance with the vacuum deposition method. In the present case, as plastics are employed those which neither combine with the dental fillings nor are partially or completely dissolved by the latter.

The advantage of using metal coated matrices resides in the simplified fabrication. Large-surface blanks of a suitable plastic are coated with the aid of metals while, at the same time, a number of uncoated surface sections are formed whose number corresponds to that of the matrices then to be stamped out from the blank, which subsequently form the windows 5. Following the coating, the matrices are then stamped out of the metal-coated blank, in which case each matrix is provided with a window-like area that-is transparent. If it is intended that every matrix is to possess several windows 5, in that case the coating process, per matrix to be stamped out, a corresponding number of transparent areas are left blank. The FIG. 18 shows a matrix 1 of a carrier or supporting material 80 of a transparent plastic which is provided with a metallic coating 81 in which one window 5 has been left blank. It is furthermore possible for the matrix 1 to be comprised of a glass metal which is inserted in the form of a thin band or film or sheet, from which the matrix 1 is fabricated while windows 5 are produced.

The number of the windows 5 constructed in the matrix 1 may be arbitrarily selected, in which case, apart from one window, the matrix 1 may be provided with two or even more than two windows disposed in side-by-side-arrangement. Especially advantageous in this connection is also a latticed construction of the metallic part of the matrix so that a plurality of windows 5 is formed which are disposed in a side-by-side arrangement or on top of each other. The inherent stability of the matrix 1 is improved by means of this design while an adequate flexibility is maintained at the same time.

The windows 5 possess a square, rectangular, circular or some other geometric configuration.

It is claimed:

1. A matrix for dental medicine for use as a formwork for fillings of light-cured plastic material to be inserted into dental cavities, the matrix comprising a band-shaped blank of transparent material, the blank having a positioning portion in a central area thereof, the central area having two ends, and two terminal areas connected to the two ends, the central area and the terminal areas having widths, the width of the central area being greater than the width of the terminal areas, the matrix further comprising a vapor-deposited coating of opaque metallic material, layered over the blank of transparent material, with at least one window portion of the transparent material free of the metallic material coating, the at least one window portion being located in the central area of the blank.

2. The matrix according to claim 1, wherein the blank has outer edges on two sides of the blank, the outer edges of the central area and of the terminal areas being in alignment on one side of the blank and the central area projecting outwardly of the outer edges of the terminal areas on the other side of the blank.

3. The matrix according to claim 1, wherein the blank of transparent material is comprised of a plastic film or sheeting.

4. The matrix according to claim 3, wherein the transparent material is cellulose acetate.

5. The matrix according to claim 1, wherein the central area of the blank has a conical shape corresponding to a cone-shaped tooth configuration, and wherein the central area comprises at least one bulge.

6. The matrix according to claim 1, wherein the blank has a longitudinal direction, comprising two window portions of the transparent material free of the metallic material coating, the two window portions being arranged next to each other in longitudinal direction of the blank.

7. The matrix according to claim 1, wherein the blank has a longitudinal direction, comprising a plurality of window portions of the transparent material free of the metallic material coating, the window portions being arranged in rows next to each other in longitudinal direction of the blank and in rows in a direction perpendicular to the longitudinal direction of the blank.

8. The matrix according to claim 1, wherein the least one window has one of a square, rectangular and circular shape.

* * * * *